United States Patent [19]

Ashimori et al.

[11] Patent Number: 4,910,195

[45] Date of Patent: Mar. 20, 1990

[54] DIHYDROPYRIDINE DERIVATIVES

[75] Inventors: Atsuyuki Ashimori; Taizo Ono; Yoshihisa Inoue, all of Kyoto; Chikara Fukaya; Kazumasa Yokoyama, both of Osaka, all of Japan

[73] Assignee: Green Cross Corporation, Osaka, Japan

[21] Appl. No.: 113,967

[22] Filed: Oct. 29, 1987

[30] Foreign Application Priority Data

Oct. 29, 1986 [JP] Japan .................. 61-257673

[51] Int. Cl.$^4$ ............ C07D 413/44; C07D 401/14; C07D 279/36; A61K 31/54
[52] U.S. Cl. .......................... 514/225.2; 514/233; 514/333; 514/334; 514/356; 514/307; 514/311; 514/338; 514/339; 544/35; 544/102; 546/257; 546/256; 546/321; 546/166; 546/148; 546/273; 546/272; 546/258
[58] Field of Search .................. 544/131, 364, 365; 546/321, 256, 257, 258, 263, 281, 193, 194, 165, 147, 273, 272, 271, 270; 514/228, 236, 253, 307, 314, 332, 333, 334, 338, 339, 343, 356

[56] References Cited

U.S. PATENT DOCUMENTS

| | | | |
|---|---|---|---|
| 4,532,248 | 7/1985 | Franckowiak et al. | 514/302 |
| 4,731,370 | 3/1988 | Watanabe et al. | 546/122 |
| 4,814,455 | 3/1989 | Poindexter | 546/273 |

FOREIGN PATENT DOCUMENTS

| | | | |
|---|---|---|---|
| 0145434 | 6/1985 | European Pat. Off. | |
| 0236838 | 9/1987 | European Pat. Off. | |
| 0247345 | 12/1987 | European Pat. Off. | |
| 0255710 | 2/1988 | European Pat. Off. | |
| 2120668 | 5/1982 | United Kingdom | 546/321 |
| 86/02640 | 5/1986 | World Int. Prop. O. | |

OTHER PUBLICATIONS

Medicinal Chemistry, 2nd Edition, 1960, pp. 565–571, 579–581, 600–601.

Primary Examiner—Jane T. Fan
Attorney, Agent, or Firm—Sughrue, Mion, Zinn, Macpeak & Seas

[57] ABSTRACT

Dihydropyridine derivatives represented by formula (I):

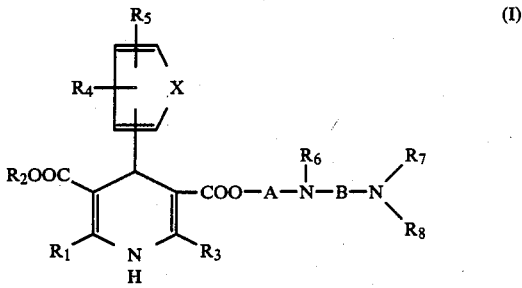

wherein $R_1$, $R_2$, $R_3$ and $R_6$, which may be the same or different, each represents an alkyl group, a cycloalkyl group or an alkoxyalkyl group; $R_4$ and $R_5$, which may be the same or different, each represents a hydrogen atom, a halogen atom, a nitro group, a halogenated alkyl group, an alkylsulfonyl group, a halogenated alkoxy group, an alkylsulfinyl group, an alkyl group, a cycloalkyl group, an alkxoy group, a cyano group, an alkoxycarbonyl group or an alkylthio group (provided that $R_4$ and $R_5$ are not hydrogen atoms at the same time); X represents a vinylene group or an azomethine group; A and B are each an alkylene group or an alkenylene group; $R_7$ and $R_8$, which may be the same or different, each represents a hydrogen atom, an alkyl group, an alkenyl group, an aralkyl group, an aryl group, or a heterocyclic group (provided that $R_7$ and $R_8$ may combine with the adjacent nitrogen atom to form a heterocyclic ring), and acid addition salts of the dihydropyridine derivatives of formula (I).

13 Claims, No Drawings

DIHYDROPYRIDINE DERIVATIVES

FIELD OF THE INVENTION

The present invention relates to novel dihydropyridine derivatives useful as pharmaceutical drugs, and acid addition salts of such derivatives.

BACKGROUND OF THE INVENTION

Nifedipine and nicardipine are known compounds, as described in U.S. Pat. Nos. 3,644,627 and 3,985,758, respectively, that are analogous to the dihydropyridine derivatives of the present invention. These compounds are known to be useful as antihypertensive agents, peripheral and cerebral vasodilators, and as coronary vasodilators (administered for the treatment of angina pectoris). However, the advent of more efficacious dihydropyridine derivatives has been desired.

SUMMARY OF THE INVENTION

An object, therefore, of the present invention is to provide dihydropyridine derivatives that have superior pharmacological activities in comparison to known compounds of this type, as well as providing corresponding acid addition salts of such derivatives.

The dihydropyridine derivatives of the present invention have high calcium-antagonistic, hypotensive, platelet agglutination inhibiting, and phosphodiesterase inhibiting activities and are useful as pharmaceutical drugs such as coronary vasodilators, cerebral blood flow enhancing agents, hypotensive agents, agents for preventing or treating thrombosis, and phosphodiesterase inhibitors.

The dihydropyridine derivatives of the present invention is represented by formula (I):

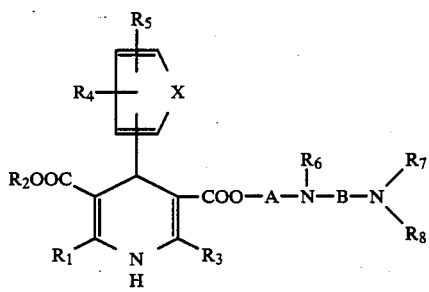

wherein $R_1$, $R_2$, $R_3$ and $R_6$, which may be the same or different, each represents an alkyl group, a cycloalkyl group or an alkoxyalkyl group; $R_4$ and $R_5$, which may be the same or different, each represents a hydrogen atom, a halogen atom, a nitro group, a halogenated alkyl group, an alkylsulfonyl group, a halogenated alkoxy group, an alkylsulfinyl group, an alkyl group, a cycloalkyl group, an alkoxy group, a cyano group, an alkoxycarbonyl group or an alkylthio group (provided that $R_4$ and $R_5$ are not hydrogen atoms at the same time); X represents a vinylene group or an azomethine group; A and B each represents an alkylene group or an alkenylene group; $R_7$ and $R_8$, which may be the same or different, each represents a hydrogen atom, an alkyl group, an alkenyl group, an aralkyl group, an aryl group, or a heterocyclic group. In addition, $R_7$ and $R_8$ may combine with the adjacent nitrogen atom to form a heterocyclic ring.

The present invention also relates to an acid addition salts of the dihydropyridine derivatives.

DETAILED DESCRIPTION OF THE INVENTION

The dihydropyridine derivatives (I) of the present invention have a unique structure compared with the dihydropyridine derivatives known in the art, and this unique structure is responsible for the increased pharmacological activities of the presently claimed compounds which are also unique. In other words, the dihydropyridine derivatives (I) and corresponding acid addition salts thereof are sharply distinguished from the conventional compounds and pharmaceutical products in that they have high organ- and tissue-selectivity in their vasodilative action, and yet still have very low levels of acute toxicity, offering very high safety levels.

The alkyl group represented by $R_1$, $R_2$, $R_3$ and $R_6$ in formula (I) may be a straight-chain or branched chain and is preferably a lower alkyl group ($C_{1-6}$) such as a methyl group, an ethyl group, a propyl group, an isopropyl group, a butyl group, an isobutyl group, a sec-butyl group, a t-butyl group, a pentyl group, an isopentyl group, a neopentyl group or a hexyl group. Particularly preferred are $C_{1-4}$ alkyl groups. These alkyl groups may have a lower cycloalkyl group ($C_{3-6}$) at the terminal and (e.g., a cyclopropylmethyl group, a cyclobutylethyl group, and a cyclopentylmethyl group). The cycloalkyl group represented by $R_1$, $R_2$, $R_3$ and $R_6$ is preferably a lower ($C_{3-6}$) cycloalkyl group such as a cyclopropyl group, a cyclobutyl group, a cyclopentyl group or a cyclohexyl group. The alkoxyalkyl group represented by $R_1$, $R_2$, $R_3$ and $R_6$ preferably has from 3 to 7 carbon atoms and includes a methoxyethyl group, an ethoxyethyl group, a propoxyethyl group, an isopropoxyethyl group, a butoxyethyl group, a methoxypropyl group, a 2-methoxy-1-methylethyl group and a 2-ethoxy-1-methylethyl group.

The substituent denoted by $R_4$ and $R_5$ may be the same or different. While this substituent may be located at any position of the ring, it is preferably situated at the 2 and/or 3 position with respect to the site where the ring is bonded to the dihydropyridine ring in formula (I). The halogen atoms represented by $R_4$ and $R_5$ include a fluorine atom, a chlorine atom, a bromine atom or an iodine atom, with the fluorine or chlorine atom being particularly preferred. Preferred examples of the alkyl groups and cycloalkyl groups represented by $R_4$ and $R_5$ may be the same as those listed above as examples of $R_1$, $R_2$, $R_3$ and $R_6$ in formula (I). The alkoxy groups and the alkylthio groups denoted by $R_4$ and $R_5$ preferably have a lower alkyl group ($C_{1-3}$) such as a methoxy group, an ethoxy group, a propoxy group or an isopropoxy group, and a methylthio group, an ethylthio group, a propylthio group or an isopropylthio groups, respectively. Examples of the alkoxycarbonyl groups represented by $R_4$ and $R_5$ are those having from 2 to 4 carbon atoms, such as a methoxycarbonyl group and an ethoxycarbonyl group. The halogen atom in the halides denoted by $R_4$ and $R_5$ has the same definition as given above for $R_4$ and $R_5$, and the halogenated alkyl group may be partially halogenated (e.g., $(CF_3)_2CHCH_2-$ and $CF_3CH_2-$) or may be totally halogenated (e.g., a trifluoromethyl group). The alkyl moiety in the halogenated alkyl group and the alkoxy moiety in the halogenated alkoxy group may be the same as those defined above for $R_1$ et al.

As in the case of the halogenated alkyl group, the halogenated alkoxy group may be partially or totally halogenated by halogen atoms. The alkyl moiety in the alkylsulfonyl group and alkylsulfinyl group denoted by $R_4$ and $R_5$ may be exemplified by those which are listed as examples of $R_1$, $R_2$, $R_3$ and $R_6$.

Preferred examples of $R_4$ and $R_5$ are a cyano group, a halogenated alkyl group (in particular, a trifluoromethyl group) and a nitro group.

The alkyl group represented by $R_7$ and $R_8$ may be illustrated by those which are listed as examples of $R_1$, $R_2$, $R_3$ and $R_6$. Preferred examples of the alkenyl group represented by $R_7$ and $R_8$ are those having $C_{3-4}$ such as an allyl group and a butenyl group. Examples of the aralkyl group represented by $R_7$ and $R_8$ are phenyl($C_{1-3}$)alkyl groups such as a benzyl group, an α-phenylethyl group, a β-phenylethyl group, and a γ-phenylpropyl group. Examples of the aryl groups represented by $R_7$ and $R_8$ include a phenyl group and a naphthyl group. These aromatic rings may have the same or different substituents at any desired position, and examples of the substituents are the same as those listed as examples of $R_4$ and $R_5$. Preferred examples of the heterocyclic group denoted by $R_7$ and $R_8$ are 5- to 7-membered rings having one or more nitrogen, sulfur or oxygen atoms as hetero atoms, and a 6-membered ring is preferred. A particularly preferable heterocyclic group is a pyridyl group such as a 2-pyridyl group, a 3-pyridyl group or a 4-pyridyl group. The heterocyclic groups may have substituents such as those listed in connection with $R_4$ and $R_5$.

The heterocyclic ring that may be formed by $R_7$ and $R_8$ may contain a hetero atom in addition to the adjacent nitrogen atom, and examples of such hetero atom include oxygen, nitrogen and sulfur atoms. Examples of the heterocyclic ring formed by $R_7$ and $R_8$ include pyrrolidine, piperidine, morpholine, piperazine, 1,2,3,4-tetrahydroquinoline, 1,2,3,4-tetrahydroisoquinoline, imidazole, indole, isoindole, benzimidazole, carbazole, phenothiazine and phenoxazine rings. These heterocyclic rings may also have substituents such as those listed in connection with $R_4$ and $R_5$.

The alkylene group represented by A and B preferably has from 2 to 12 carbon atoms, and the alkenylene group represented by A and B preferably has from 4 to 12 carbon atoms. The alkylene group and the alkenylene group may be a straight-chain or a branched chain; the alkylene group may be exemplified by an ethylene group, a trimethylene group, a tetramethylene group and a 1,2-dimethylethylene group, and the alkenylene group but a butenylene group and a pentenylene group.

The ring represented by

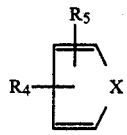

which is the substituent at the 4-position of the dihydropyridine ring in formula (I) is a benzene ring when X is a vinylene group (—CH=CH—) and is a pyridine ring when X is an azomethine group (—CH=N—). The benzene ring or pyridine ring may be bonded at any position thereof to the 4-position of the dihydropyridine ring.

While $R_4$ and $R_5$ may be bonded to this ring at any position, they are preferably situated on the position ortho and/or meta to the carbon on the ring which is bonded to the 4-position of the dihydropyridine ring.

The dihydropyridine derivatives (I) of the present invention may be prepared by reacting a certain compound representing a portion of formula (I) with a compound representing the remaining portion by means of the reaction which mechanisms are known per se, in particular, dehydrocyclization. An illustrative process for the production of dihydropyridine derivatives (I) is set forth below:

Production process

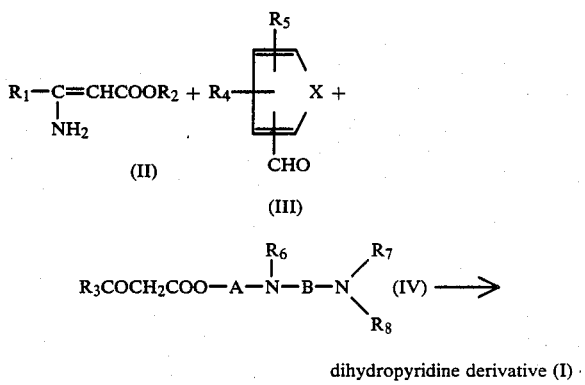

dihydropyridine derivative (I)

wherein $R_1$, $R_2$, $R_3$, $R_4$, $R_5$, $R_6$, $R_7$, $R_8$, X, A and B have the same meanings as defined above for formula (I).

The reaction of compound (II) with compounds (III) and (IV) is usually carried out at temperatures between about 20° and 160° C., preferably between about 30° and 130° C. Any solvent that is inert to the reaction may be employed, and examples thereof include alkanols such as methanol, ethanol, propanol, isopropanol, butanol and sec-butanol; ethers such as ethyl ether, dioxane, tetrahydrofuran, ethylene glycol monomethyl ether and ethylene glycol dimethyl ether; acetic acid; pyridine; as well as N,N-dimethylformamide, dimethyl sulfoxide and acetonitrile. The compounds (II), (III) and (IV) are reacted in amounts such that any two of them are each 1 to 1.5 moles per mole of the third compound. The reaction generally takes 1 to 30 hours for its completion.

Compounds of formula (IV) which are used as one of the starting materials may be synthesized in accordance with the following reaction scheme 1:

Reaction Scheme 1

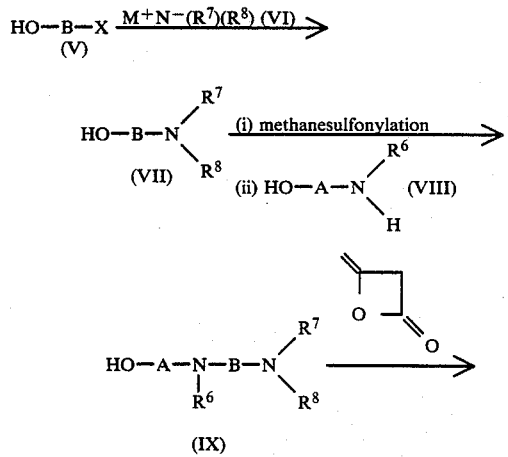

-continued
Reaction Scheme 1

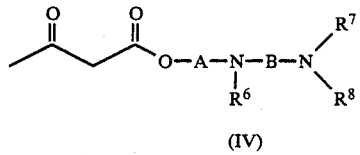

wherein X is halogen other than fluorine; $M^+$ is an appropriate alkali metal ion; and $R_6$, $R_7$, $R_8$, A and B are the same as defined above for formula (I).

The reaction between compounds (V) and (VI) is generally carried out in a suitable solvent that does not contain any acidic protons that will react with compound (VI). Examples of the solvents include ethers such as diethyl ether, tetrahydrofuran and dioxane; aromatic hydrocarbons such as benzene, toluene and xylene; and aprotic polar solvents such as N,N-dimethylformamide, dimethyl sulfoxide, hexamethylphosphoric triamide and N-methylpyrrolidone. A suitable alkali metal is used as $M^+$ in compound (VI), and examples thereof include lithium, sodium and potassium. Compound (VI) is generally used in an amount of at least about 2 moles, preferably about 2 to 2.5 moles, per mole of compound (V). The reaction between compounds (V) and (VI) is generally performed at about $-76°$ to $40°$ C. and is typically completed in about 10 minutes to 24 hours. The resulting compound (VII) is subjected to a reaction that is known per se, for example, methanesulfonylation with methanesulfonyl chloride (see A. Fürst and Pl. A. Plattner, Helv, 32, 275 (1949)), followed by reaction with compound (VIII), preferably in a suitable solvent, in the presence of a suitable inorganic or organic base, thereby producing compound (IX). Suitable solvents include halogenated hydrocarbons such as methylene chloride and chloroform; esters such as methyl acetate and ethyl acetate; ethers such as monoglyme, diglyme and triglyme; and aprotic polar solvents such as N,N-dimethylformamide, dimethyl sulfoxide, hexamethylphosphoric triamide and N-methylpyrrolidone. Useful inorganic bases include sodium carbonate, sodium hydrogen carbonate, potassium carbonate, potassium hydrogen carbonate, calcium carbonate and magnesium carbonate. Suitable organic bases include triethylamine, pyridine and 4-dimethylaminopyridine. Compound (VIII) is used in an amount equal or in excess to that of compound (VII). The reaction between compounds (VII) and (VIII) is generally carried out at temperatures between about 0° and 200° C., preferably between about 20° and 150° C., and usually takes 10 minutes to 24 hours for its completion.

The resulting compound (IX) is reacted with diketene in a suitable solvent, preferably in the presence of a catalyst, so as to produce the compound (IV). Suitable catalysts include: basic compounds such as organic bases (e.g., triethylamine, pyridine, 4-dimethylaminopyridine and N,N-dimethylaniline) and inorganic bases (e.g., sodium acetate and potassium carbonate); and acidic compounds such as sulfonic acid (e.g., p-toluenesulfonic acid) and Lewis acids (e.g., boron trifluoride). Examples of solvents include: aromatic compounds such as benzene, toluene and xylene; esters such as methyl acetate and ethyl acetate; halogenated hydrocarbons such as methylene chloride and chloroform; ethers such as diethyl ether, tetrahydrofuran, dioxane, monoglyme, diglyme and triglyme; and aprotic polar solvents such as N,N-dimethylformamide, N,N-dimethylacetamide, N-methylpyrrolidone and dimethyl sulfoxide. Diketene may be used in an amount equal or in excess to that of compound (IX), and preferably 1 to 2 equivalents of diketene is used. The reaction between diketene and compound (IX) is generally performed at temperatures between about $-20°$ and $200°$ C., preferably between about $-10°$ to $120°$ C., and is usually completed in about 5 minutes to 24 hours.

The dihydropyridine derivatives (I) contain a basic group in their structure, and thus may be converted to an acid addition salt by known techniques. Any pharmaceutically acceptable acid addition salts may be formed, and examples thereof are salts with inorganic acids (e.g., hydrochlorides, hydrobromides, phosphates and sulfates) and salts with organic acids (e.g., acetates, succinates, maleates, fumarates, malates, and tartrates).

The so prepared novel dihydropyridine derivatives (I) or acid addition salts thereof may be subjected to known techniques of isolation and purification (such as concentration, extraction, chromatography, reprecipitation and recrystallization used either alone or in combination) to be recovered as products of any desired purity.

If the dihydropyridine derivatives (I) or acid addition salts thereof are to be used as a pharmaceutical drugs, they may be mixed with pharmaceutically necessary ingredients such as appropriately selected pharmacologically acceptable additives (e.g., carriers, excipients and diluents), formulated as pharmaceutical compositions in desired dosage forms such as powders, granules, tablets, capsules and injections, and administered either orally or parenterally. In these pharmaceutical preparations, dihydropyridine derivatives (I) or acid addition salts thereof are incorporated in their effective amounts. The dosage varies with such factors as the route of administration, the severity of the disease to be treated, the weight of the patient and his age. In the case of oral administration to an adult hypertensive patient, a dihydropyridine derivative (I) or acid addition salt thereof is preferably administered daily in one to several portions in an amount of about 0.05 to 20 mg/kg body weight, more preferably 0.1 to 4 mg/kg body weight.

The dihydropyridine derivatives (I) of the present invention and acid addition salts thereof are very low in their toxicity and yet exhibit strong and persistent hypotensive action, as well as peripheral, coronary and cerebral vasodilative actions, in mammals (e.g., mice, rats, rabbits, dogs, cats and humans). Therefore, there novel compounds are useful as drugs for preventing and treating circulatory diseases in humans, such as hypertension, ischemic cardiac diseases (e.g., angina pectoris and myocardial infarction), and cerebral and peripheral disorders (e.g., cerebral infraction and transient ischemic attack).

EXPERIMENTAL PROCEDURES AND RESULTS (1) Hypotensive effects

An experiment was conducted to investigate the hypotensive effects of the dihydropyridine derivatives (I) and acid addition salts thereof on 10- to 11-week-old male rats (3 to 5 animals per group).

For blood pressure determination, systolic pressure was measured without anesthesia by an indirect tail-cuff method using a sphygmomanometer (PE-300, Narco Bio-System).

Each of the test compounds was suspended in 10% HCO-60 (polyoxyethylated castor oil produced by Nikko Chemicals K.K.) and administered orally to the animals in a dose of 10 mg/kg. Blood pressure measurements were conducted at predetermined time intervals. As a result, it was found that the dihydropyridine derivatives (I) of the present invention and acid addition salts thereof exhibited marked hypotensive effects in a persistent manner over a prolonged period.

The novel compounds provided by the present invention attained a maximum blood pressure fall of 15 to 31% compared with 20% for nicardipine. The 50% recovery time (i.e., the time required for the reduced blood pressure to return to half the maximal reduction) ranged from 1.3 to 18 hours compared with 3.1 hours for nicardipine.

(2) Acute toxicity

The $LD_{50}$ was estimated with the use of male mice (3 to 5 mice per a group) at the age of 10 to 11 weeks, weighing 14 to 16 g. The results were at least more than 1100 mg/kg and those of most test compounds were more than 1400 mg/kg.

Accordingly, the compounds which the present invention provides are significantly lower in their acute toxicity than known compounds and thus safer.

The following examples are provided for the purpose of further illustrating the present invention but are in no way to be taken as limiting. Unless otherwise noted, $CDCl_3$ was used as a solvent in $^1H$-NMR analyses.

EXAMPLE 1

Preparation of 2-[N-methyl-N-(2-diphenylaminoethyl)amino]ethyl methyl 2,6-di-methyl-4-(4-cyano-2-pyridyl)-1,4-dihydropyridine-3,5-dicarboxylate and monofumarate thereof A 50-ml eggplant type flask was charged with 1.003 g (7.59 mmol) of 4-cyano-2-pyridinealdehyde, 2.691 g (7.59 mmol) of 2-[N-methyl-N-(2-diphenylaminoethyl)amino]ethyl acetoacetate and 901 mg (7.59 mmol) of methyl 3-aminocrotonate. After addition of isopropanol (10 ml), the contents were dissolved therein. The flask was equipped with a Dimroth condenser and the solution was heated at 40° to 45° C. for 39 hours with agitation. The reaction solvent was tilled off under reduced pressure and the residue (6.175 g) was fractionated by column chromatography on silica gel (elution solvent: ethyl acetate/methanol=99:1). The resulting crude product was recrystallized from isopropyl ether/methanol so as to obtain a pale yellow powder of the desired compound in an amount of 2.219 g (yield: 59%). m.p. (after crystallization from isopropanol ether/methanol): 155.5° to 157° C. Pertinent IR and NMR data are as follows and are provided for each of the compounds and acid addition salts described in the following Examples as well.

$IR\nu_{max}^{KBr} cm^{-1}$:

2250 (CN), 1705 (C=O) 1665 (C=O)

$^1H$—NMR δ:

8.61 (1H, d, J = 5Hz, 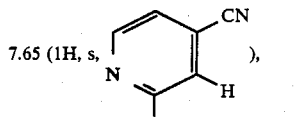 ), 7.65 (1H, s, 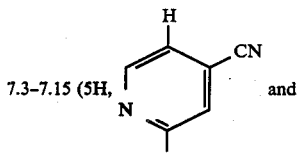 ), 7.3-7.15 (5H, 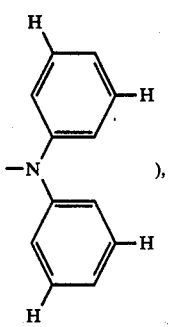 and 7.05-6.85 (7H, 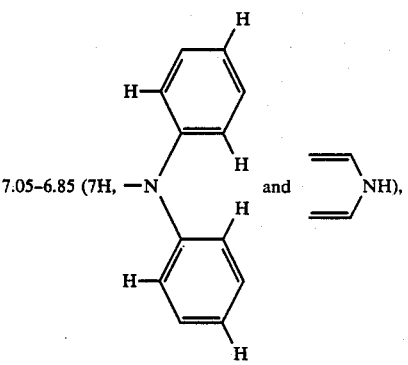 and =NH), 5.22 (1H, s, $C_4$—H), 4.10 (2H, t, J = 6Hz, —$CO_2 \underline{CH_2CH_2}$N<), 3.85-3.7 (2H, >N$\underline{CH_2CH_2}$N< ), 3.60 (3H, s, $CH_3CO$—), 2.75-2.5 (4H, —$\underline{CH_2}$N$\underline{CH_2CH_2}$N< ), 2.30, 2.28 (each 3H, s, $C_2$— and $C_6$—$CH_3$)

2.26 (3H, s, >N$CH_3$)

The above-obtained compound (2.090 g, 3.69 mmol) was placed in a 300-ml eggplant type flask. After addition of ethanol (168 ml), the contents were dissolved therein. Thereafter, fumaric acid (429 mg, 3.69 mmol) was added and the flask was equipped with an air-cooling tube. After continued agitation at room temperature for 1.5 hours, the reaction solvent was distilled off under reduced pressure to obtain a slightly yellow powder of a fumarate of the desired compound in an amount of about 2.5 g.

$IR\nu_{max}^{KBr}$ cm$^{-1}$:

3300 (CO<u>OH</u>), 2500 (—$\overset{+}{N}$H—O$_2$C<), 2200 (CN), 1685 (C=O)

$^1$H—NMR $\delta_{DMSO\text{-}d6}$:

8.93 (1H, s, >NH), 8.66 (1H, d, J = 5Hz, [pyridine with CN]), 7.59 (1H, s, [pyridine with CN]), 7.56 (1H, dd, J = 5, 1.5 Hz, [pyridine with CN]), 7.3–7.15 (4H, —N(phenyl)$_2$), 7.0–6.85 (6H, —N(phenyl)$_2$), 6.63 (2H, s, $^-$O$_2$C—CH=CH—CO$_2$H), 5.09 (1H, s, C$_4$—H), 4.1–4.0 (2H, —COOCH$_2$CH$_2$N<), 3.85–3.7 (2H, >NCH$_2$CH$_2$N<), 3.49 (3H, s, CH$_3$CO—), 2.7–2.55 (4H, —CH$_2$CH$_2$NH$_2$CH$_2$N<), 2.26 (6H, s, C$_2$— and C$_6$—CH$_3$)

2.24 (3H, s, >NCH$_3$).

EXAMPLE 2

Preparation of 2-[N-methyl-N-(2-phenothiazine-10-ylethyl)amino]ethyl methyl 2,6-dimethyl-4-(3-nitrophenyl)-1,4-dihydropyridine-3,5-dicarboxylate and monofumarate thereof A 30-ml eggplant type flask was charged with 768 mg (5.08 mmol) of m-nitrobenzaldehyde, 1.954 g (5.08 mmol) of 2-[N-methyl-N-(2-phenothiazine-10-ylethyl)amino]ethyl acetoacetate and 603 mg 5.08 mmol) of methyl 3-aminocrotonate. After addition of isopropanol (7.5 ml), the flask was equipped with a Dimroth condenser and the contents were refluxed for 21 hours under heating. The reaction solvent was distilled off under reduced pressure and the residue (3.336 g) was fractionated by column chromatography on silica gel (eluting solvent: ethyl acetate/n-hexane=3:1) to obtain a purified organge yellow powder of the desired compound in an amount of 1.977 g (yield: 63%).

$IR\nu_{max}^{KBr}$ cm$^{-1}$:

1665 (C=O), 1520 (NO$_2$), 1345 (NO$_2$)

$^1$H—NMR $\delta$:

8.19 (1H, s, [nitrophenyl]), 8.05 (1H, ddd, J = 8; 1; 1Hz, [nitrophenyl])

7.73 (1H, d, J = 8Hz, [nitrophenyl]), 7.41 (1H, d, J = 8Hz, [nitrophenyl]),

-continued 7.25–7.15 (4H, 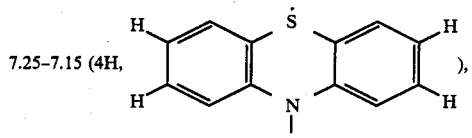 ), 7.05–6.9 (4H, 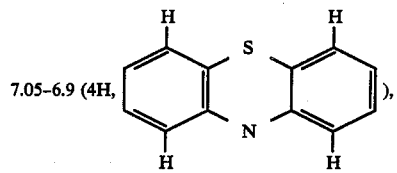 ), 6.05 (1H, s, 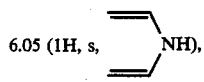 ), 5.20 (1H, s, C$_4$—H), 4.22 (2H, t, J = 6Hz, 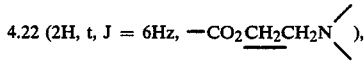 ), 4.02 (2H, t, J = 6.5Hz, 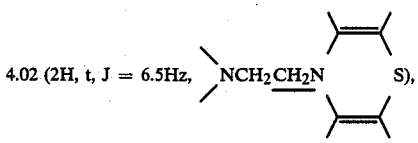 ), 3.70 (3H, s, CH$_3$CO—), 2.87 (2H, t, J = 6.5Hz, 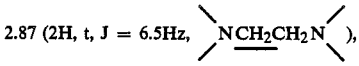 ), 2.76 (2H, t, J = 6Hz, 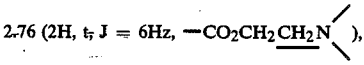 ), 2.43 (3H, s, 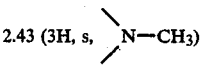 )

2.41 (6H, s, C$_2$—, and C$_6$—CH$_3$)

The above-obtained compound (1.862 g, 3.03 mmol) was placed in a 100-ml eggplant type flask. After addition of ethanol (45 ml), the contents were dissolved therein. Thereafter, fumaric acid (325 mg, 3.03 mmol) was added and the flask was equipped with an air-cooling tube. After continued agitation at room temperature for 2 hours, the reaction solvent was distilled off under reduced pressure to obtain a yellow powder of a fumarate of the desired compound in an amount of about 2.2 g.

IR$\nu_{max}^{KBr}$ cm$^{-1}$:

3300 (COOH), 2500 (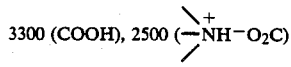)

1690 (C=O), 1525 (NO$_2$), 1360 (NO$_2$)

$^1$H—NMR $\delta_{DMSO-d6}$:

9.03 (1H, s, 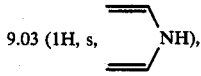 ),

-continued 8.0–7.9 (2H, 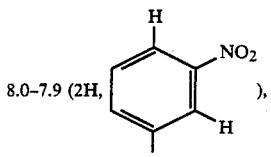 ), 7.61 (1H, d, J = 8Hz, 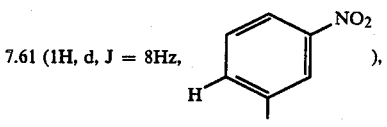 ), 7.47 (1H, t, J = 8Hz, 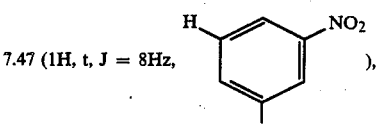 ), 7.2–7.05 (4H, 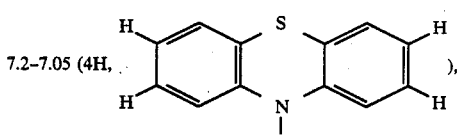 ), 7.05–6.85 (4H, 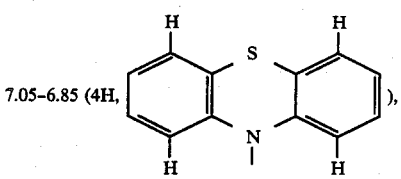 ), 6.61 (2H, s, 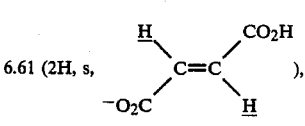 ), 4.99 (1H, s, C$_4$—H), 4.03 (2H, t, J = 5.5Hz, 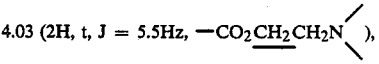 ), 3.90 (2H, t, J = 6Hz, 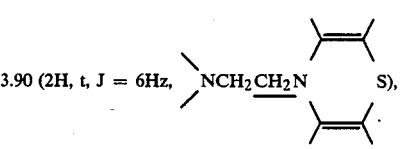 ), 3.50 (3H, s, CH$_3$CO—)

2.75–2.55 (4H, 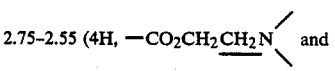 and

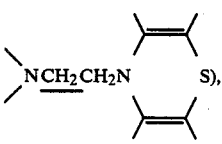 ), 2.28 (3H, s, 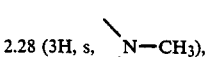 ), 2.26 (6H, s, C$_2$— and C$_6$—CH$_3$)

EXAMPLE 3

Preparation of 2-[N-methyl-N-(4-phenothiazin-10-ylbutyl)amino]ethyl methyl 2,6-dimethyl-4-(3-nitrophenyl)-1,4-dihydropyridine-3,5-dicarboxylate and monofumarate thereof A 50-ml eggplant type flask was charged with 1.029 g (6.81 mmol) of m-nitrobenzaldehyde, 2.810 g (6.81 mmol) of 2-[N-methyl-N-(4-phenothiazin-10-ylbutyl)amino]ethyl acetoacetate, and 808 mg (6.81 mmol) of methyl-3-aminocrotonate. After addition of isopropanol (10 ml), the flask was equipped with a Dimroth condenser and the contents were refluxed for 20 hours under heating, followed by agitation at 45° C. for 40 hours. Thereafter, the reaction solvent was distilled off under reduced pressure and the residue (4.617 g) was fractionated and purified by column chromatography on silica gel twice (first eluting solvent: ethyl acetate/methanol=99:1; second eluting solvent: chloroform/methanol=96:4). As a result, an organge yellow powder of the desired compound was obtained in an amount of 1.370 g (yield: 31%).

IR$\nu_{max}^{KBr}$ cm$^{-1}$: 1680 (C=O), 1525 (NO$_2$), 1345 (NO$_2$)

$^1$H—NMR δ: 8.17 (1H, t, J=2Hz, 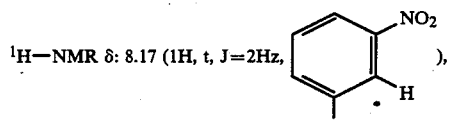 ), 8.05 (1H, ddd, J=8; 2; 1Hz, 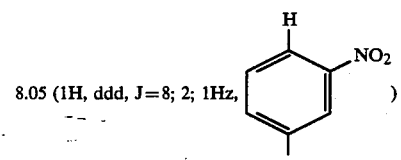 )

7.72 (1H, dt, J=8; 1Hz, 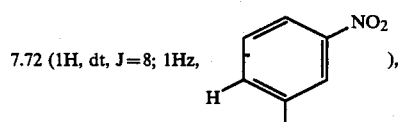 ), 7.41 (1H, t, J=8Hz, 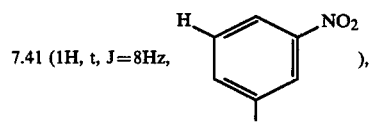 ), 7.25–7.15 (4H, 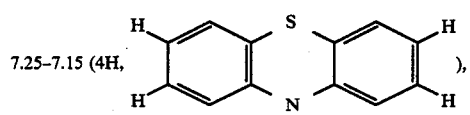 ), 7.0–6.9 (4H, 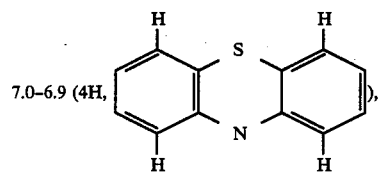 ), 6.02 (1H, s, 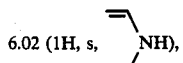NH), 5.17 (1H, s, C$_4$—H), 4.17 (2H, t, J=6Hz, —CO$_2$CH$_2$CH$_2$N⟨ ), 3.94 (2H, t, J=7Hz, ⟩NCH$_2$CH$_2$CH$_2$CH$_2$—), 3.70 (3H, t, CH$_3$CO—), 2.63 (2H, t, J=6Hz, —CO$_2$CH$_2$CH$_2$N⟨ ), 2.62 (2H, t, J=7Hz, ⟩NCH$_2$CH$_2$CH$_2$CH$_2$—), 2.42, 2.39 (each 3H, s, C$_2$— and C$_6$—CH$_3$), 2.25 (3H, s, ⟩N—CH$_3$), 1.88 (2H, quint., J=7Hz, ⟩NCH$_2$CH$_2$CH$_2$CH$_2$—), 1.64 (2H, quint., J=7Hz, ⟩NCH$_2$CH$_2$CH$_2$CH$_2$—)

The above-obtained compound (1.277 g, 1.99 mmol) was placed in a 200-ml eggplant type flask. After addition of ethanol (50 ml), the contents were dissolved therein. Thereafter, fumaric acid (231 mg, 1.99 mmol) was added and the flask was equipped with an air-cooling tube. After continued stirring for 1.5 hours at room temperature, the reaction solvent was distilled off under reduced pressure to obtain a yellow powder of a fumarate of the desired compound in an amount of about 1.5 g.

IR$\nu_{max}^{KBr}$ cm$^{-1}$: 3350 (C<u>OOH</u>), 2550 (—$\overset{+}{\text{NH}}$—O$_2$C)
1690 (C=O), 1525 (NO$_2$), 1345 (NO$_2$)

$^1$H—NMR δ$_{DMSO-d6}$: 9.05 (1H, s, 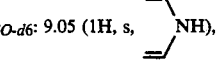NH), 8.0–7.9 (2H, 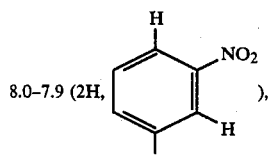 ), 7.63 (1H, d, J=8Hz, 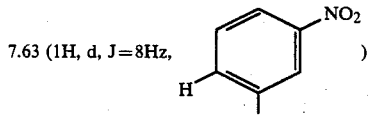 )

-continued 7.48 (1H, t, J=8Hz, 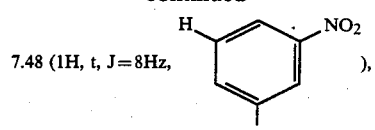), 7.25–7.05 (4H, 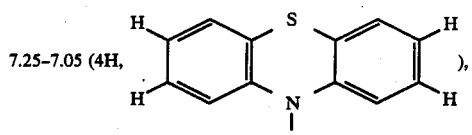), 7.05–6.85 (4H, 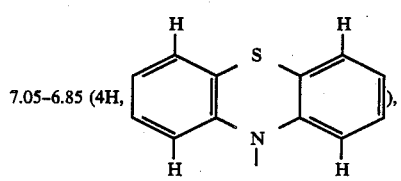), 6.61 (2H, s, 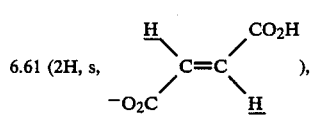), 5.00 (1H, s, C$_4$—H), 4.1–4.0 (2H, —CO$_2$CH$_2$CH$_2$N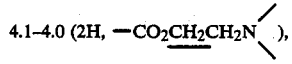), 3.86 (2H, t, J=6.5Hz, NCH$_2$CH$_2$CH$_2$CH$_2$—), -continued 3.54 (3H, s, CH$_3$CO—), 2.7–2.6 (2H, —COOCH$_2$CH$_2$N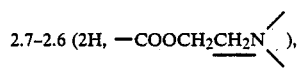), 2.5–2.4 (2H, NCH$_2$CH$_2$CH$_2$CH$_2$—), 2.30 (6H, s, C$_2$— and C$_6$—CH$_3$), 2.22 (3H, s, 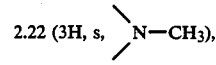N—CH$_3$), 1.8–1.4 (4H, NCH$_2$CH$_2$CH$_2$CH$_2$—),

EXAMPLES 4 TO 17

Compounds having the structures shown in Tables 1-1 to 1-4 below were synthesized in accordance with the procedures described in Examples 1 to 3. Table 1 also lists the melting points, nature and appearance of the thus-synthesized compounds, as well as the nature and appearance of their respective salts. The NMR and IR data of the thus-synthesized compounds are given in Tables 2-1 to 2-10 below. Unless otherwise noted, the NMR data were obtained by using CDCl$_3$ as a solvent.

TABLE 1-1

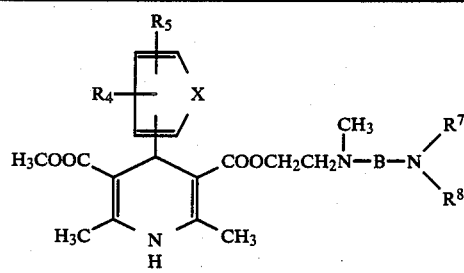

| Example No. | R$_4$—[ring with R$_5$, X] | B | —NR$_7$R$_8$ | mp, Nature and Appearance | Salt | Nature and Appearance |
|---|---|---|---|---|---|---|
| 4 | NC-pyridyl (with CH$_3$) | —CH$_2$CH$_2$— | —N(CH$_2$Ph)$_2$ | 143–154° C. (chloroform/isopropyl ether) pale yellow powder | fumarate | pale yellow powder |

TABLE 1-1-continued $$\text{Structure: H}_3\text{COOC and COOCH}_2\text{CH}_2\text{N}(\text{CH}_3)\text{—B—N}(R^7)(R^8) \text{ groups on 1,4-dihydro-2,6-dimethylpyridine with R}_4, R_5, X \text{ substituted ring}$$

| Example No. | Ring (R4, R5, X) | B | —NR7R8 | mp, Nature and Appearance | Salt | Nature and Appearance |
|---|---|---|---|---|---|---|
| 5 | 4-CN-pyridin-2-yl | " | phenothiazin-10-yl (—N with two benzene rings fused via S) | 176–178° C. (chloroform/methanol) pale yellow powder | fumarate | pale yellow powder |
| 6 | 4-CN-pyridin-2-yl | —CH₂CH₂CH₂— | phenothiazin-10-yl | 147–149° C. (isopropyl ether/methanol) pale yellow powder | fumarate | pale yellow powder |
| 7 | 4-CN-pyridin-2-yl | —CH₂CH₂— | carbazol-9-yl | 157–160° C. (isopropyl ether/methanol) pale yellow powder | fumarate | pale yellow powder |
| 8 | 3-methyl-2-CF₃-pyridin-... | —CH₂CH₂— | N,N-diphenylamino | yellow powder (amorphous) | fumarate | pale yellow powder |

TABLE 1-1-continued $$\text{Structure: } H_3COOC-\overset{R_4\overset{R_5}{\diagup}X}{\underset{H_3C\underset{H}{\overset{N}{\diagup}}CH_3}{\diagdown}}-COOCH_2CH_2\overset{CH_3}{\underset{}{N}}-B-N\overset{R^7}{\underset{R^8}{\diagdown}}$$

| Example No. | (R4/R5/X ring) | B | —NR7R8 | mp, Nature and Appearance | Salt | Nature and Appearance |
|---|---|---|---|---|---|---|
| 9 | pyridine with CF3 and CH3 | " | —N(CH2-phenyl)2 | pale yellow oil | fumarate | pale yellow powder |
| 10 | pyridine with CF3 and CH3 | " | phenothiazin-10-yl (—N with two benzene rings fused via S) | pale yellow oil | fumarate | pale yellow powder |
| 11 | pyridine with CF3 and CH3 | —CH2CH2CH2— | phenothiazin-10-yl | pale yellow oil | fumarate | pale yellow powder |
| 12 | pyridine with CF3 and CH3 | —CH2CH2— | carbazol-9-yl | pale yellow oil | fumarate | pale yellow powder |

TABLE 1-1-continued

Structure:
H3COOC—[dihydropyridine core with R4, R5, X substituents]—COOCH2CH2N(CH3)—B—N(R7)(R8)
with H3C, CH3 at 2,6 positions and N-H

| Example No. | [R4/R5/X group] | B | —NR7R8 | mp, Nature and Appearance | Salt | Nature and Appearance |
|---|---|---|---|---|---|---|
| 13 | 3-NO2-phenyl | " | —N(phenyl)2 | pale yellow oil | fumarate | pale yellow powder |
| 14 | 3-NO2-phenyl | —CH2CH2CH2— | phenothiazin-10-yl | orange powder (amorphous) | fumarate | pale yellow powder |
| 15 | 3-NO2-phenyl | —(CH2)6— | phenothiazin-10-yl | yellow oil | fumarate | pale yellow powder |
| 16 | 3-NO2-phenyl | —(CH2)8— | phenothiazin-10-yl | yellow oil | fumarate | pale yellow powder |

TABLE 1-1-continued

Structure:
$H_3COOC$ and $COOCH_2CH_2N(CH_3)-B-N(R^7)(R^8)$ substituents on a 1,4-dihydropyridine with 2,6-dimethyl and N-H, with R_4/R_5/X cyclic substituent at 4-position.

| Example No. | (R_4/R_5/X group) | B | —NR_7R_8 | mp, Nature and Appearance | Salt | Nature and Appearance |
|---|---|---|---|---|---|---|
| 17 | 3-nitrophenyl | —(CH_2)_{12}— | phenothiazine (—N...S ring) | yellow oil | fumarate | pale yellow powder |

TABLE 2

| Example No. | H-NMR σ | IR ν$_{max}$ cm$^{-1}$ |
|---|---|---|
| 4 | 8.59(1H, d, J=5.0Hz, [3-cyano-pyridyl]), 7.62(1H, s, [pyridyl-H]), 7.16–7.37(11H, [pyridyl-H and phenyl H×2]), 6.88(1H, s, NH), 5.18(1H, s, C$_4$—H), 4.06(2H, t, J=6.0Hz, —CO$_2$CH$_2$CH$_2$—), 3.61(4H, s, —N(CH$_2$-φ)$_2$), 3.59(3H, s, —CO$_2$CH$_3$), 2.56(4H, NCH$_2$CH$_2$N), 2.53(2H, t, J=6.0Hz, —CO$_2$CH$_2$CH$_2$N), 2.24, 2.27(each 3H, s, C$_2$— and C$_6$—CH$_3$), 2.17(3H, s, NCH$_3$). | 2225(CN), 1705(C=O), 1665(C=O) (KBr) |
| 4 fumarate | 8.94(1H, NH), 8.66(1H, d, J=4.9Hz, [pyridyl]), 7.56–7.59(2H, [pyridyl-H]), 7.19–7.44(10H, phenyl H×2), 6.61(2H, s, —O$_2$C—CH=CH—CO$_2$H), 5.06(1H, s, C$_4$—H), 4.03(2H, —CO$_2$CH$_2$CH$_2$—), 3.55(4H, —N(CH$_2$-φ)$_2$), 3.51(3H, —CO$_2$CH$_3$), 2.50–2.61(6H, —CH$_2$NCH$_2$CH$_2$N), 2.16, 2.23(each 3H, s, C$_2$— and C$_6$—CH$_3$), 2.05(3H, s, NCH$_3$). (DMSO-d$_4$) | 2225(CN), 1690(C=O) (KBr) |

TABLE 2-continued

| Example No. | H-NMR σ | IR$\nu_{max}$ cm$^{-1}$ |
|---|---|---|
| 5 | 8.60(1H, d, J=5Hz, [NC-pyridyl]), 7.63(1H, s, [NC-pyridyl]), 7.27(1H, d, J=5Hz, [NC-pyridyl]), 7.2–7.05(4H, [phenothiazine aromatic]), 6.95–6.7(4H, [phenothiazine aromatic]), 6.75(1H, s, NH), 5.22(1H, s, C$_4$—H), 4.15(2H, t, J=5.5Hz, —CO$_2$CH$_2$CH$_2$N<), 4.01(2H, t, J=6.5Hz, >NCH$_2$CH$_2$), 3.61(3H, s, —CO$_2$CH$_3$), 2.87(2H, t, J=6.5Hz, >NCH$_2$CH$_2$), 2.74(2H, t, J=5.5Hz, —CO$_2$CH$_2$CH$_2$N<), 2.41(3H, s, >NCH$_3$), 2.30, 2.27(each 3H, s, C$_2$— and C$_6$—CH$_3$). | 2225(CN), 1700(C=O), 1665(C=O) (KBr) |

TABLE 2-continued

| Example No. | H-NMR σ | IRν$_{max}$ cm$^{-1}$ |
|---|---|---|
| 5 fumarate | 8.94(1H, s, [pyridine-NH]), 8.66(1H, dd, J=5; 1Hz, [pyridine]), 7.60(1H, [pyridine]), 7.57(1H, dd, J=5; 1.5Hz, [pyridine]), 7.25–7.1(4H, [phenothiazine ring H]), 7.1–6.85(4H, [phenothiazine ring H]) (DMSO—d$_4$), 6.65(2H, s, $^-O_2C-CH=CH-CO_2H$), 5.11(1H, s, C$_4$—H), 4.06(2H, brs, —CO$_2$CH$_2$CH$_2$N<), 3.97(2H, t, J=6Hz, >NCH$_2$CH$_2$N<), 3.51(3H, s, —CO$_2$CH$_3$), 2.78(2H, t, J=6Hz, >NCH$_2$CH$_2$N<), 2.70(2H, t, J=5Hz, —CO$_2$CH$_2$CH$_2$N<), 2.34(3H, s, >N—CH$_3$), 2.26, 2.25(each 3H, s, C$_2$— and C$_6$—CH$_3$). | 3300(COC<u>H</u>), 2500(>N$^+$H$^-$O$_2$C), 2225(CN), 1690(C=O) (KBr) |

TABLE 2-continued

| Example No. | H-NMR σ | IR$\nu_{max}$ cm$^{-1}$ |
|---|---|---|
| 6 | 8.60(1H, d, J=5Hz, [structure]), 7.62(1H, s, [structure]), 7.27(1H, dd, J=5; 1Hz, [structure]), 7.2-7.0(4H, [structure]), 6.95-6.8(4H, [structure]), 5.19(1H, s, C$_4$—H), 4.06(2H, t, J=6Hz, —CO$_2$CH$_2$CH$_2$N<), 3.89(2H, t, J=7Hz, >NCH$_2$CH$_2$N<), 3.59(2H, s, —CO$_2$CH$_3$), 2.54(2H, t, J=6Hz, —CO$_2$CH$_2$CH$_2$N<), 2.50(2H, t, J=7Hz, >NCH$_2$CH$_2$N<), 2.26, 2.24(each 3H, s, C$_2$— and C$_6$—CH$_3$), 2.21(3H, s, >N—CH$_3$), 1.90(2H, quint, >NCH$_2$CH$_2$CH$_2$N< [structure]). | 2225(CN), 1700(C=O), 1665(C=O) (KBr) |

TABLE 2-continued

| Example No. | H-NMR σ | IRν$_{max}$ cm$^{-1}$ |
|---|---|---|
| 6 fumarate | 8.94(1H, s, [pyridine-CN structure] NH), 8.67(1H, d, J=5.5Hz, [pyridine-CN structure]), 7.56(1H, d, J=5.5Hz, [pyridine-CN structure]), 7.56(1H, s, [pyridine-CN structure]), 7.25–7.1(4H, [phenothiazine aromatic H]), 7.05–6.85(4H, [phenothiazine aromatic H]), 6.62(2H, s, $^-O_2C-CH=CH-CO_2H$), 5.08(1H, s, C$_4$—H), 4.05(2H, t, J=6Hz, —CO$_2$CH$_2$CH$_2$N⟨phenothiazine⟩), 3.88(2H, t, J=7Hz, ⟩NCH$_2$CH$_2$N), 3.51(3H, s, —CO$_2$CH$_3$), 2.64(2H, t, J=6Hz, —CO$_2$CH$_2$CH$_2$N⟨phenothiazine⟩), 2.59(2H, t, J=7Hz, ⟩NCH$_2$CH$_2$N), 2.24(9H, s, C$_2$—, C$_4$—CH$_3$ and ⟩NCH$_3$), 1.84(2H, quint, J=7Hz, ⟩NCH$_2$CH$_2$N) (DMSO—d$_6$) | 3300(C=O), 2500(⟩N$^+$H—O$_2$C), 2225(CN), 1690(C=O) (KBr) |

TABLE 2-continued

| Example No. | H-NMR σ | IR$\nu_{max}$ cm$^{-1}$ |
|---|---|---|
| 7 | 8.56(1H, dd, J=5; 1Hz, [pyridine-CN]), 8.07(2H, dt, J=8; 1Hz, [phenyl]), 7.64(1H, s, [pyridine-CN]), 7.44(2H, td, J=8; 1Hz, [phenyl]), 7.41(2H, dd, J=8; 1Hz, [phenyl]), 7.3-7.15(3H, [phenyl and pyridine-CN]), 6.78(1H, s, [phenyl], NH), 5.21(1H, s, C$_4$—H), 4.36(2H, t, J=7.5Hz, >NCH$_2$CH$_2$N<), 4.12(2H, t, J=6Hz, —CO$_2$CH$_2$CH$_2$N<), 3.58(3H, s, —CO$_2$CH$_3$), 2.80(2H, t, J=7.5Hz, >NCH$_2$CH$_2$N<), 2.68(2H, t, J=6Hz, —CO$_2$CH$_2$CH$_2$N<), 2.40(3H, s, >NCH$_3$), 2.23, 2.28(each 3H, s, C$_2$— and C$_6$—CH$_3$). | 2225(CN), 1700(C=O), 1665(C=O), (KBr) |

TABLE 2-continued

| Example | | |
|---|---|---|
| No. | H-NMR σ | IR$\nu_{max}$ cm$^{-1}$ |
| 7 fumarate | 8.94(1H, s, [pyridine-NC fragment] NH), 8.66(1H, dd, J=5; 1Hz,), 8.14(2H, d, J=7.5Hz, [carbazole fragment]), 7.65-7.5(4H, [biphenyl-pyridine fragment] and), 7.43(2H, t, J=7.5Hz,), 7.19(2H, t, J=7.5Hz, [carbazole fragment]), 6.66(2H, s, $^{-}O_2C-CH=CH-CO_2H$), 5.12(1H, s, $C_4-H$), 4.45(2H, t, J=7Hz, >NCH$_2$CH$_2$N<), 4.15-3.95(2H, $-CO_2CH_2CH_2N<$), 3.50(3H, s, $-CO_2CH_3$), 2.78(2H, t, J=7Hz, >NCH$_2$CH$_2$N<), 2.68(2H, t, J=5.5Hz, $-CO_2CH_2CH_2N<$), 2.33(3H, s, >NCH$_3$), 2.27, 2.24(each 3H, s, $C_2-$ and $C_6-CH_3$). (DMSO-$d_4$) | 3300(C=O), 2450(>N$^+$H$^-$O$_2$C), 2225(CN), 1690(C=O) (KBr) |

TABLE 2-continued

| Example No. | H-NMR σ | IRν$_{max}$ cm$^{-1}$ |
|---|---|---|
| 8 | 8.56(1H, d, J=4.5Hz, [pyridine-CF$_3$]), 7.98(1H, d, J=8Hz, [pyridine-CF$_3$]), 7.43(1H, dd, J=8; 4.5Hz, [pyridine-CF$_3$]), 7.4–7.25(4H, [benzene H×2]), 7.15–6.95(6H, [benzene H×2], NH), 5.91(1H, s, C$_4$—H), 5.68(1H, s, C$_4$—H), 4.4–4.1(2H, m, —CO$_2$CH$_2$CH$_2$N<), 3.83(2H, t, J=7.5Hz, >NCH$_2$CH$_2$N<), 3.66(3H, s, —CO$_2$CH$_3$), 2.8–2.6(4H, —CO$_2$CH$_2$CH$_2$NCH$_2$—), 2.40, 2.39(each 3H, s, C$_2$— and C$_6$—CH$_3$), 2.33(3H, s, >N—CH$_3$). | 1700(C=O) (KBr) |
| 8 fumarate | 8.98(1H, s, NH), 8.47(1H, d, J=4Hz, [pyridine-CF$_3$]), 7.92(1H, d, J=8Hz, [pyridine-CF$_3$]), 7.57(1H, dd, J=8; 4Hz, [pyridine-CF$_3$]), 7.25(4H, t, J=8Hz, [benzene H×2]), 7.05–6.85(6H, [benzene H×2]), 6.64(2H, s, —O$_2$C—CH=CH—CO$_2$H), 5.42(1H, s, C$_4$—H), 4.2–3.9(2H, m, —CO$_2$CH$_2$CH$_2$N<), 3.74(2H, t, J=7Hz, >NCH$_2$CH$_2$N<), 3.45(3H, s, —CO$_2$CH$_3$), 2.65–2.5(4H, —CH$_2$NCH$_2$CH$_2$N<), 2.26(6H, s, C$_2$— and C$_6$—CH$_3$), 2.22(3H, s, >N—CH$_3$). (DMSO—d$_4$) | 3300(COO$\underline{H}$), 2600($\underset{\smile}{\supset}$N$^+$H—O$_2$C), 1690(C=O) (KBr) |

TABLE 2-continued

| Example No. | H-NMR σ | IR ν$_{max}$ cm$^{-1}$ |
|---|---|---|
| 9 | 8.49(1H, d, J=3.6Hz, [2-CF₃-pyridyl]), 7.89(1H, d, J=8.0Hz, [2-CF₃-pyridyl]), 7.15–7.39(11H, [2-CF₃-pyridyl] and [phenyl H×2], 5.69(1H, s, NH), 5.59(1H, s, C₄—H), 4.14–4.26 and 3.87–3.99(2H, ABm, —CO₂CH₂—), 3.583, 3.575(7H, overlapped —COCH₃ and —N(CH₂-φ)₂), 2.52(6H, s, CH₂NCH₂CH₂N[piperazine]), 2.28, 2.31(each 3H, s, C₂— and C₆—CH₃), 2.13(3H, s, >NCH₃). | 1700(C=O) (KBr) |
| 9 fumarate | 8.98(1H, s, NH), 8.48(1H, d, J=4.1; 7.2Hz, [2-CF₃-pyridyl]), 7.57(1H, dd, J=4.1; 7.2Hz, [2-CF₃-pyridyl]), 7.91(1H, d, J=7.2Hz, [2-CF₃-pyridyl]), 7.19–7.32(10H, m, [phenyl H×2]), 6.61(2H, s, [fumarate ⁻O₂C-CH=CH-CO₂H]), 5.42(1H, s, C₄—H), 4.08–4.14 and 3.87–3.93(2H, ABm, —CO₂CH₂—), 3.53(4H, s, —N(CH₂-φ)₂), 3.45(3H, s, —CO₂CH₃), 2.46–2.59(6H, —CH₂NCH₂CH₂N[piperazine]), 2.24, 2.25(each 3H, s, C₂— and C₆—CH₃), 2.12(3H, s, >NCH₃). (DMSO—d₆) | 1700(C=O) (KBr) |

TABLE 2-continued
| Example No. | H-NMR σ | IR ν$_{max}$ cm$^{-1}$ |
|---|---|---|
| 10 | 8.55(1H, d, J=4.3Hz, 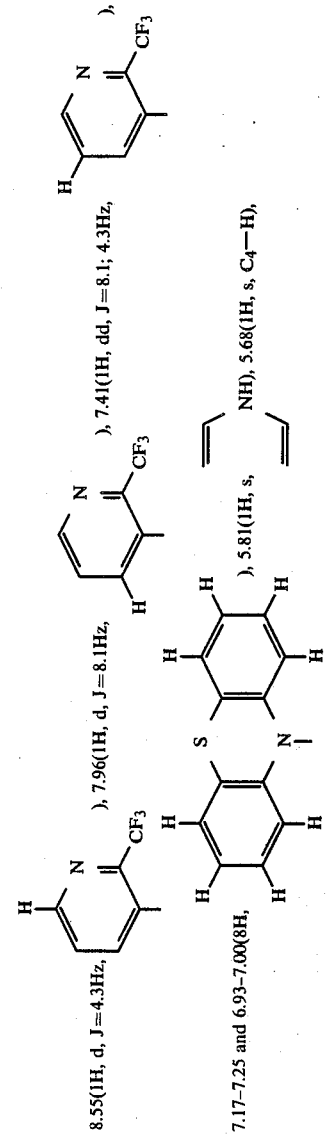), 7.96(1H, d, J=8.1Hz, ), 7.41(1H, dd, J=8.1; 4.3Hz, ...), 7.17-7.25 and 6.93-7.00(8H, ...), 5.81(1H, s, NH), 5.68(1H, s, C$_4$—H), 4.26-4.38 and 4.07-4.19(2H, ABm, —CO$_2$CH$_2$—), 3.91-3.99(2H, m, —CH$_2$N ...), 2.66-2.86(4H, m, —CH$_2$NCH$_2$—), 2.39(9H, C$_2$—, C$_4$—CH$_3$ and ...NCH$_3$). | 1700(C=O) (KBr) |

TABLE 2-continued

| Example No. | H-NMR σ | IRν$_{max}$ cm$^{-1}$ |
|---|---|---|
| 10 fumarate | 8.95(1H, s, [pyridine-CF$_3$ group] NH), 8.46(1H, d, J=4.1Hz, [pyridine-CF$_3$ group]), 7.90(1H, d, J=7.8Hz, [pyridine-CF$_3$ group]), 7.55(1H, dd, J=7.8; 4.1Hz, [pyridine-CF$_3$ group]), 7.11–7.20 and 6.89–7.03(8H, [phenothiazine group]), 6.64(2H, s, [fumarate -O$_2$C-CH=CH-CO$_2$H]), 5.41(1H, s, C$_4$—H), 4.04-4.16 and 3.92-4.01(2H, ABm, —CO$_2$CH$_2$—), 3.88(2H, t, J=6.4Hz, —CH$_2$N[dihydropyridine]), 3.45(3H, s, —CO$_2$CH$_3$), 2.69(2H, t, J=6.4Hz, ›NCH$_2$CH$_2$N‹), 2.59(2H, t, J=5.7Hz, —CO$_2$CH$_2$CH$_2$N‹), 2.25(9H, C$_2$—, C$_4$—CH$_3$ and ›NCH$_3$). (DMSO—d$_4$) | 1700(C=O) (KBr) |

TABLE 2-continued
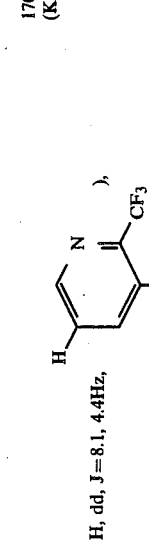

TABLE 2-continued

| Example No. | H-NMR σ | IR$\nu_{max}$ cm$^{-1}$ |
|---|---|---|
| 11 fumarate | 8.96(1H, s, [pyridyl-CF$_3$ NH]), 8.48(1H, d, J=4.0Hz, [pyridyl-CF$_3$]), 7.91(1H, d, J=7.2Hz, [pyridyl-CF$_3$]), 7.57(1H, dd, J=7.2, 4.0Hz, [pyridyl-CF$_3$]), 6.89–7.00 and 7.07–7.22(8H, m, [diphenylsulfide-N]), 6.62(2H, s, [fumarate −O$_2$C−CH=CH−CO$_2$H]), 5.42(1H, s, C$_4$−H), 4.04–4.16 and 3.85–3.97(2H, ABm, −CO$_2$CH$_2$−), 3.84(2H, t, J=7.0Hz, −CH$_2$N S), 3.45(3H, s, −CO$_2$CH$_3$), 2.47–2.57(4H, −CH$_2$NCH$_2$CH$_2$N⟨), 2.24(6H, s, C$_2$− and C$_6$−CH$_3$), 2.17(3H, s, ⟩NCH$_3$), 1.77(2H, quint, J=7.0Hz, ⟩NCH$_2$CH$_2$CH$_2$N⟨). (DMSO−d$_6$) | 1700(C=O) (KBr) |

TABLE 2-continued
| Example No. | H-NMR σ | IRν$_{max}$ cm$^{-1}$ |
|---|---|---|
| 12 | 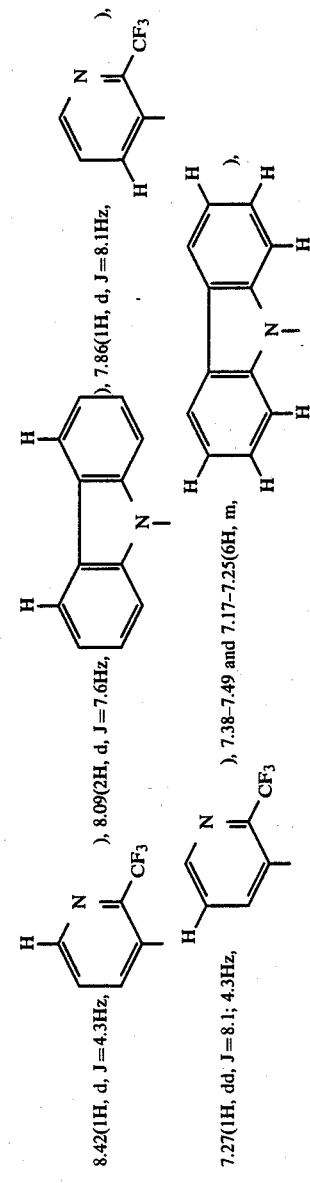 | 1700(C=O) (KBr) |

TABLE 2-continued

| Example No. | H-NMR σ | IR ν_max cm⁻¹ |
|---|---|---|
| 12 fumarate | 8.96(1H, s, [allyl-NH-allyl] NH), 8.44(1H, d, J=4.2Hz, [pyridine-CF3]), 8.13(2H, d, 7.7Hz, [phenyl-NH]), 7.90(1H, d, J=7.6Hz, [pyridine-CF3]), 7.15–7.57(7H, [biphenyl and pyridine-CF3]), 6.64(2H, s, $^-O_2C-CH=CH-CO_2H$), 3.86–4.11(2H, ABm, —CO₂CH₂—), 3.45(3H, s, —CO₂CH₃), 2.70(2H, t, J=7.0Hz, >NCH₂CH₂N<), 2.59(2H, t, J=5.8Hz, —CO₂CH₂CH₂N<), 2.24–2.26(9H, s, C₂—, C₆—CH₃ and >NCH₃). (DMSO-d₆) | 1700(C=O) (KBr) |
| 13 | 8.10(1H, t, J=2Hz, [nitrophenyl]), 7.97(1H, dd, J=8, 2Hz, [nitrophenyl]), 7.65(1H, d, J=8Hz, [nitrophenyl]), 7.4–7.25(5H, [nitrophenyl]×2), 7.05–6.9(6H, H×2), 6.00(1H, s, NH), 5.11(1H, s, C₄—H), 4.11(2H, t, J=6Hz, —CO₂CH₂CH₂N<), 3.80(2H, t, J=7.5Hz, >NCH₂CH₂N<), 3.61(3H, s, —CO₂CH₃), 2.75–2.6(4H, —CH₂NCH₂CH₂N<), 2.35, 2.34(each 3H, s, C₂— and C₆—CH₃), 2.28(3H, s, >NCH₃). | 1690(C=O), 1520(NO₂), 1350(NO₂) (CHCl₃) |

TABLE 2-continued

| Example No. | H-NMR σ | IR ν$_{max}$ cm$^{-1}$ |
|---|---|---|
| 13 fumarate | 9.06(1H, s, ![structure with NH and NO2]NH), 8.0–7.9(2H, ![structure]), 7.63(1H, d, J=8Hz, ![structure]), 7.49(1H, t, J=8Hz, ![structure]), 7.23(4H, t, J=8Hz, ![structure] H×2), 7.0–6.85(6H, ![structure] H×2), 6.63(2H, s, $^-O_2C-\underline{H}C=C\underline{H}-CO_2H$), 5.01(1H, s, C$_4$—H), 4.05(2H, t, J=5.5Hz, —CO$_2$CH$_2$CH$_2$N⟩), 3.77(2H, t, J=7Hz, ⟩NCH$_2$CH$_2$N⟩), 3.51(3H, s, —CO$_2$CH$_3$), 2.75–2.55(4H, —CH$_2$N<u>C</u>H$_2$CH$_2$N⟩), 2.30, 2.29(each 3H, s, C$_2$— and C$_6$—CH$_3$), 2.24(3H, s, ⟩NCH$_3$). (DMSO d$_6$) | 3300(COOH), 2500⟩N$^+$H—O$_2$C) 1685(C=O), 1525(NO$_2$), 1345(NO$_2$)(KBr) |

TABLE 2-continued

| Example No. | H-NMR σ | IR ν$_{max}$ cm$^{-1}$ |
|---|---|---|
| 14 | 8.18(1H, t, J=2Hz, [structure with NO$_2$]), 8.05(1H, ddd, J=8, 2, 1Hz, [structure with NO$_2$]), 7.72(1H, d, J=8Hz, [structure with NO$_2$]), 7.41(1H, d, J=8Hz, [structure with NO$_2$]), 7.3-7.1(4H, [structure]), 7.05-6.85(4H, [structure]), 6.03(1H, s, NH), 5.18(1H, s, C$_4$—H), 4.16(2H, t, J=6Hz, —CO$_2$CH$_2$N[structure]), 3.97(2H, t, J=7Hz, [structure]NCH$_2$CH$_2$CH$_2$N[structure]), 3.69(3H, s, —CO$_2$CH$_3$), 2.7-2.5(4H, —CH$_2$NCH$_2$CH$_2$N[structure]), 2.42, 2.40(each 3H, s, C$_2$— and C$_6$—CH$_3$), 2.27(3H, s, >NCH$_3$), 1.97(2H, quint, J=7Hz, [structure]NCH$_2$CH$_2$N[structure]) | 1680(C=O), 1525(NO$_2$), 1345(NO$_2$) (KBr) |

TABLE 2-continued

| Example No. | H-NMR σ | IR ν$_{max}$ cm$^{-1}$ |
|---|---|---|
| 14 fumarate | 9.05(1H, s, ![structure with NO2 and NH], NH), 8.0–7.9(2H, ![structure with NO2]), 7.63(1H, d, J=8Hz, ![structure with NO2]), 7.48(1H, t, J=8Hz, ![structure with NO2]), 7.2–7.05(4H, ![diphenyl sulfide N structure]), 7.05–6.85(4H, ![diphenyl sulfide N structure]), 6.63(2H, s, ![fumarate -O2C-CH=CH-CO2H]), 5.01(1H, s, C$_4$—H), 4.05(2H, t, J=5Hz, —CO$_2$CH$_2$CH$_2$N<), 3.87(2H, t, J=6.5Hz, >NCH$_2$CH$_2$N<), 3.52(3H, s, —CO$_2$CH$_3$), 2.7–2.45(4H, —CH$_2$NCH$_2$CH$_2$N<), 2.29(6H, s, C$_2$— and C$_4$—CH$_3$), 2.22(3H, s, >NCH$_3$), 1.82(2H, quint, J=6.5Hz, >NCH$_2$CH$_2$CH$_2$N<) (DMSO—d$_6$) | 3350(COOH), 2550(>N$^+$H—O$_2$C), 1685(C=O), 1520(NO$_2$), 1345(NO$_2$)(KBr) |

TABLE 2-continued

| Example No. | H-NMR σ | IR $\nu_{max}$ cm$^{-1}$ |
|---|---|---|
| 15 | 8.10(1H, t, J=2Hz, [Ar-NO2]), 7.98(1H, ddd, J=8;2;2Hz, [Ar]), 7.64(1H, dd, J=8;1Hz, [Ar-NO2]), 7.34(1H, t, J=8Hz, [Ar]), 7.2–7.05(4H, [phenothiazine]), 6.95–6.8(4H, [phenothiazine]), 5.97(1H, s, NH), 5.10(1H, s, C$_4$—H), 4.11(2H, t, J=6Hz, —CO$_2$CH$_2$CH$_2$N<), 3.83(2H, t, J=7Hz, —CH$_2$N<), 3.62(3H, s, —CO$_2$CH$_3$), 2.55(2H, td, J=6;2Hz, —CO$_2$CH$_2$CH$_2$N<), 2.35–2.2(2H, —CO$_2$CH$_2$CH$_2$NCH$_2$—), 2.32, 2.33(each 3H, s, C$_2$— and C$_6$—CH$_3$), 2.18(3H, s, >NCH$_3$), 1.85–1.7(2H, —CH$_2$CH$_2$N<), 1.5–1.15(6H, >NCH$_2$CH$_2$CH$_2$CH$_2$CH$_2$N<) | 1695(C=O), 1520(NO$_2$), 1350(NO$_2$) (CHCl$_3$) |

TABLE 2-continued

| Example No. | H-NMR σ | IR$\nu_{max}$ cm$^{-1}$ |
|---|---|---|
| 15 fumarate | 9.06(1H, s, NH), 8.05–7.9(2H, [3-NO2-phenyl-H]), 7.64(1H, d, J=7.5Hz, [Ar-H]), 7.55–7.4(1H, [Ar-H]), 7.25–7.05(4H, [phenothiazine-H]), 7.05–6.85(4H, [phenothiazine-H]), 6.61(2H, s, $^-O_2C$–CH=CH–$CO_2H$ fumarate), 4.10(2H, t, J=5.5Hz, –CO$_2$CH$_2$CH$_2$N<), 3.84(2H, t, J=6.5Hz, –CH$_2$N<), 3.54(3H, s, –CO$_2$CH$_3$), 2.70(2H, t, J=5.5Hz, –CO$_2$CH$_2$CH$_2$N<), 2.5–2.35(2H, –CO$_2$CH$_2$CH$_2$NCH$_2$–), 2.31, 2.30(each 3H, s, C$_2$– and C$_6$–CH$_3$), 2.25(3H, s, >NCH$_3$), 1.75–1.55(2H, –CH$_2$CH$_2$N<), 1.45–1.1(6H, >NCH$_2$(CH$_2$)$_3$CH$_2$CH$_2$N<) (DMSO–d$_6$) | 3350(COOH), 2600(>N$^+$H$^-$O$_2$C), 1690(C=O), 1525(NO$_2$), 1345(NO$_2$), (KBr) |

TABLE 2-continued

| Example No. | H-NMR σ | IR$\nu_{max}$ cm$^{-1}$ |
|---|---|---|
| 16 | 8.10(1H, t, J=2Hz, [3-NO2-phenyl]), 7.98(1H, ddd, J=8;2.5;2.5Hz, [NO2-phenyl]), 7.65(1H, dt, J=8;1.5Hz, [NO2-phenyl]), 7.35(1H, t, J=8Hz, [NO2-phenyl]), 7.2-7.05(4H, [phenothiazine ring]), 6.95-6.8(4H, [phenothiazine ring]), 5.96(1H, s, NH), 5.11(1H, s, C4—H), 4.12(2H, t, J=6.5Hz, —CO2CH2CH2N<), 3.83(2H, t, J=7Hz, —CH2N<), 3.63(3H, s, —CO2CH3), 2.57(2H, td, J=6.5;2Hz, —CO2CH2CH2N<), 2.34(6H, s, C2— and C6—CH3), 2.20(3H, s, >NCH3), 1.9-1.7(2H, >N(CH2)6CH2CH2N<), 1.5-1.1(10H, >NCH2(CH2)5CH2CH2N<). | 1690(C=O), 1520(NO2), 1350(NO2), (CHCl3) |

TABLE 2-continued

| Example No. | H-NMR σ | IR $\nu_{max}$ cm$^{-1}$ |
|---|---|---|
| 16 fumarate | 9.06(1H, s, NH), 8.05–7.95(2H, [3-NO2-phenyl]), 7.7–7.6(1H, [2-NO2-phenyl]), 7.55–7.45(1H, [4-NO2-phenyl]), 7.25–7.05(4H, [nitrophenyl]), 7.05–6.85(4H, [diphenyl sulfide/amine]), 6.61(2H, s, $^{-}O_2C-CH=CH-CO_2H$), 5.02(1H, s, C$_4$—H), 4.12(2H, t, J=5.5Hz, —CO$_2$CH$_2$CH$_2$N<), 3.84(2H, t, J=7Hz, —CH$_2$N<), 3.54(3H, s, —CO$_2$CH$_3$), 2.72(2H, t, J=5.5Hz, —CO$_2$CH$_2$CH$_2$N<), 2.5–2.4(2H, —CO$_2$CH$_2$CH$_2$NCH$_2$—), 2.31, 2.30(each 3H, s, C$_2$ and C$_6$—CH$_3$), 2.27(3H, s, >NCH$_3$), 1.8–1.6(2H, —CH$_2$CH$_2$N<), 1.5–1.1(10H, >NCH$_2$(CH$_2$)$_5$CH$_2$N<) (DMSO-d$_6$) | 3350(COOH), 2500(>N$^+$H···$^-$O$_2$C), 1690(C=O), 1525(NO$_2$), 1345(NO$_2$), (KBr) |

TABLE 2-continued

| Example No. | H-NMR σ | IRν$_{max}$ cm$^{-1}$ |
|---|---|---|
| 17 | 8.18(1H, t, J=2Hz, [3-nitrophenyl]), 8.07(1H, ddd, J=8;2,2Hz, [nitrophenyl]), 7.74(1H, d, J=8Hz, [nitrophenyl]), 7.44(1H, t, J=8Hz, [nitrophenyl]), 7.18-7.22(4H, [diphenyl sulfide/amine]), 6.91-7.01(4H, [diphenyl sulfide/amine]), 6.01(1H, s, NH), 5.19(1H, s, C$_4$—H), 4.21(2H, t, J=6Hz, —CO$_2$CH$_2$CH$_2$N[pip]), 3.91(2H, t, J=7Hz, —CH$_2$N[pip]), 3.72(3H, s, —CO$_2$CH$_3$), 2.66(2H, td, J=6;2Hz, —CO$_2$CH$_2$CH$_2$N[pip]), 2.37-2.43(8H, C$_2$—CH$_3$, C$_6$—CH$_3$ and —CO$_2$CH$_2$CH$_2$NCH$_2$—), 2.30(3H, s, N[pip]NCH$_3$), 1.80-1.94(2H, —CH$_2$CH$_2$—N[pip]), 1.40-1.53(6H, —CH$_2$CH$_2$CH$_2$N[pip]), 1.32(14H, s, —(CH$_2$)$_7$CH$_2$CH$_2$CH$_2$N[pip]) | 1700(C=O), (KBr) |

TABLE 2-continued

| Example No. | H-NMR σ | IR ν$_{max}$ cm$^{-1}$ |
|---|---|---|
| 17 fumarate | 9.08(1H, s, NH), 7.96–7.98(2H, ), 7.62(1H, d, J=8Hz, ), 7.45–7.53(1H, ),<br>7.08–7.20(4H, ), 6.85–6.97(4H, ), 6.57(2H, s, ), 4.99(1H, s,<br>C$_4$—H), 4.11(2H, t, J=5Hz, —CO$_2$CH$_2$CH$_2$N⟨ ⟩), 3.81(2H, t, J=7Hz, —CH$_2$N⟨ ⟩), 3.52(3H, s, —CO$_2$CH$_3$),<br>2.6–2.8(2H, —CO$_2$CH$_2$CH$_2$N⟨ ⟩), 2.37–2.50(2H, ⟩NCH$_2$(CH$_2$)$_{11}$N⟨ ⟩),<br>2.26, 2.71, 2.29(each 3H, s, C$_2$—CH$_3$, C$_6$—CH$_3$ and ⟩NCH$_3$), 1.57–1.70(2H, —CH$_2$CH$_2$N⟨ ⟩),<br>1.0–1.4(20H, ⟩NCH$_2$(CH$_2$)$_{10}$CH$_2$N⟨ ⟩).<br>(DMSO—d$_4$) | 1700(C=O).<br>(KBr) |

While the invention has been described in detail and with reference to specific embodiments thereof, it will be apparent to one skilled in the art that various changes and modifications can be made therein without departing from the spirit and scope thereof.

What is claimed is:

1. A dihydropyridine represented by formula (I):

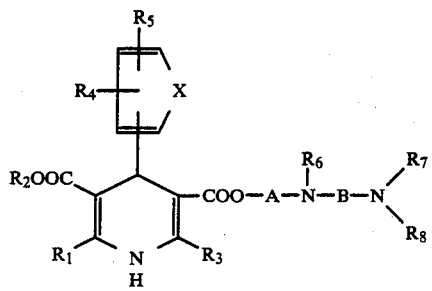

wherein $R_1$, $R_2$, $R_3$ and $R_6$, which may be the same or different, each represents a $C_{1-6}$ alkyl group, a $C_{3-6}$ cycloalkyl group or a $C_{3-7}$ alkoxyalkyl group; $R_4$ and $R_5$, which may be the same or different, each represents a hydrogen atom, a halogen atom, a nitro group, a halogenated $C_{1-6}$ alkyl group, a $C_{1-6}$ alkylsulfonyl group, a halogenated $C_{1-3}$ alkoxy group, a $C_{1-6}$ alkylsulfinyl group, a $C_{1-6}$ alkyl group, a $C_{3-6}$ cycloalkyl group, a $C_{1-3}$ alkoxy group, a cyano group, a $C_{2-4}$ alkoxycarbonyl group or a $C_{1-6}$ alkylthio group (provided that $R_4$ and $R_5$ are not hydrogen atoms at the same time); X represents a vinylene group or an azomethine group; A and B are each a $C_{2-12}$ alkylene group or a $C_{4-12}$ alkenylene group; $R_7$ and $R_8$, which may be the same or different, each represents a hydrogen atom, a $C_{3-4}$ alkenyl group, a naphthyl group, a pyridyl group or $R_7$ and $R_8$ may combine with the adjacent nitrogen atom to form a heterocyclic ring that comprises a 1,2,3,4-tetrahydroquinoline, 1,2,3,4-tetrahydroisoquinoline, imidazole, indole, isoindole, benzimidazole, carbazole, phenothiazine or phenoxazine ring.

2. Acid addition salt of the dihydropyridine of claim 1.

3. Dihydropyridine derivative or acid addition salt thereof according to claim 1 or 2, wherein A is an ethylene group.

4. Dihydropyridine derivative or acid addition salt thereof according to claim 1 or 2, wherein X is an azomethine group.

5. Dihydropyridine derivative or acid addition salt thereof according to claim 1 or 2, wherein X is a vinylene group.

6. Dihydropyridine or acid addition salt thereof according to claim 1 or 2, wherein said acid addition salt is a salt with an inorganic acid selected from a hydrochloride, a hydrobromide, a phosphate and a sulfate.

7. Dihydropyridine or acid addition salt thereof according to claim 1 or 2, wherein said acid addition salt is a salt with an organic acid selected from an acetate, a succinate, a maleate, a fumarate, a maleate and a tartrate.

8. Dihydropyridine or acid addition salt thereof according to claim 2, wherein $R_4$ is a hydrogen atom, $R_5$ is selected from the group consisting of $NO_2$, $CF_3$ and $CN$, and

is selected from the group consisting of phenothiazinyl and carbazolyl.

9. Dihydropyridine according to claim 1, wherein

is a phenothiazinyl group or a carbazolyl group.

10. Dihydropyridine according to claim 1, wherein X is a vinylene group, $R_4$ is a hydrogen atom, $R_5$ is a nitro group, wherein

is selected from the group consisting of phenothiazinyl and carbazolyl.

11. Dihydropyridine according to claim 1, wherein X is an azomethine group, $R_4$ is a hydrogen atom, $R_5$ is a cyano group,

is selected from the group consisting of phenothiazinyl and carbazolyl.

12. Dihydropyridine acccording to claim 1, wherein X is an azomethine group, $R_4$ is a hydrogen atom, $R_5$ is a trifluoromethyl group,

is selected from the group consisting of phenothiazinyl and carbazolyl.

13. A pharmaceutical composition comprising an effective amount of a dihydropyridine or acid addition salt thereof according to claim 1 or claim 2 in an amount effective for treating coronary artery disease, peripheral and cerebral artery disease or hypertension and a pharmaceutically acceptable diluent.

* * * * *